(12) United States Patent
Gomes

(10) Patent No.: US 6,432,145 B1
(45) Date of Patent: Aug. 13, 2002

(54) OXIDATION HAIR DYEING AGENT COMPOSITION

(75) Inventor: Alvaro Luiz Gomes, Sao Paulo (BR)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 09/837,243

(22) Filed: Apr. 18, 2001

(51) Int. Cl.⁷ ................................................. A61K 7/13
(52) U.S. Cl. ....................... 8/405; 8/406; 8/407; 8/410; 8/581
(58) Field of Search ........................... 8/405, 406, 407, 8/410, 581

(56) References Cited

U.S. PATENT DOCUMENTS

| | | | |
|---|---|---|---|
| 5,654,362 A | 8/1997 | Schulz et al. | 524/862 |
| 5,690,697 A | 11/1997 | Samain | 8/423 |
| 5,811,487 A | 9/1998 | Schulz et al. | 524/862 |
| 5,880,210 A | 3/1999 | Schulz et al. | 524/731 |
| 5,969,035 A | 10/1999 | Meinhardt et al. | 524/731 |
| 6,240,929 B1 * | 6/2001 | Richard et al. | 132/202 |

FOREIGN PATENT DOCUMENTS

GB    2138845    10/1984

* cited by examiner

*Primary Examiner*—Lorna M. Douyon
*Assistant Examiner*—Eisa Elhilo
(74) *Attorney, Agent, or Firm*—Jim L. De Cesare

(57) ABSTRACT

An oxidation hair dyeing agent composition provides a color tone for dyed hair which is not easily affected by repeated washing with cold and hot water containing shampoo and soap, and it has superior wash resistance. The oxidation hair dyeing agent composition is characterized as containing a cyclic silicone and a silicone elastomer. As a two-component type oxidation hair dyeing agent composition, it contains as the first component a mixture of an oxidation dye precursor, a cyclic silicone, a silicone elastomer, an emulsifying agent, and water. The mixture is emulsified in water using the emulsifying agent. The second component of the composition is an aqueous hydrogen peroxide solution.

6 Claims, No Drawings

OXIDATION HAIR DYEING AGENT COMPOSITION

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention is directed to an oxidation hair dyeing agent composition containing silicones, and more specifically relates to oxidation hair dyeing agent compositions of superior washing resistance containing a cyclic silicone and a silicone elastomer.

BACKGROUND OF THE INVENTION

Oxidation hair dyeing agents are most widely used as permanent hair dyeing agents. Oxidation dye precursors in such hair dyeing agents penetrate into hair, and chemically impart a color to the hair by means of color formation resulting from oxidative polymerization under the action of an oxidation agent. The process is generally one characterized by permanency in the dyeing effect.

As far as the forms of such oxidation hair dyeing agents are concerned, numerous two-component type products are known. They are used by mixing, at the time of hair dyeing, a first agent containing an oxidation dye precursor, and a second agent containing an oxidation agent. There are also single-component products which are powder-like. These products are used by mixing the one component with water at the time of hair dyeing. Multi-component products containing three or more agents are also known.

Hair dyeing agents containing silicones are known, and reference may be had, for example, to Japanese Kokai Patent Application Publication No. Sho 59[1984]-190910/British Patent 2138845 (October 1984), which describes a process for dyeing hair using a hair dyeing agent composition containing a silicone derivative obtained by introducing tertiary amino groups or quaternary ammonium groups into the side chain of polydiorganosiloxanes to produce deep color tones. Japanese Kokai Patent Application Publication No. Hei 08[1996]-040851 also discloses an oxidation hair dyeing agent composition, but it contains a saccharide derivative and a silicone. The silicone is exemplified by dimethylpolysiloxane, amino-modified polysiloxane, epoxy-modified polysiloxane, and a polyether-modified polysiloxane.

However, the problem with such compositions is that even if hair is dyed with such hair dyeing agent compositions, the color tone of the dyed hair tends to fade when hair is repeatedly washed with cold and hot water containing shampoo and soap.

BRIEF SUMMARY OF THE INVENTION

It is therefore an object of the invention to eliminate the disadvantages of previously known oxidation hair dyeing agent compositions, and provide an oxidation hair dyeing agent composition in which color tones of dyed hair are not easily affected by repeated washing with cold and hot water containing shampoo and soap, and which has superior wash resistance.

Accordingly, it was unexpectedly discovered that an oxidation hair dyeing agent composition containing a cyclic silicone and a silicone elastomer had superior hair dyeing ability, it produced no dye color irregularities, and it possessed superior washing resistance.

These and other features of the invention will become apparent from a consideration of the detailed description.

BRIEF DESCRIPTION OF THE SEVERAL VIEWS OF THE DRAWING

Not applicable.

DETAILED DESCRIPTION OF THE INVENTION

The present invention relates to an oxidation hair dyeing agent composition, and it is generally characterized by the fact that it contains a cyclic silicone and a silicone elastomer. More particularly, a two-component type oxidation hair dyeing agent composition is provided, and it contains as a first agent or component a mixture of an oxidation dye precursor, a cyclic silicone, a silicone elastomer, an emulsifying agent, and water. This mixture is emulsified in water using the emulsifying agent. The second agent or component of the composition is an aqueous hydrogen peroxide solution.

The cyclic silicones used in the oxidation hair dyeing agent compositions of the invention are known in the cosmetic industry under The Cosmetic, Toiletry, and Fragrance Association (CTFA) name CYCLOMETHICONE. Reference may be had to the CTFA's International Cosmetic Ingredient Dictionary. Some representative examples are octamethylcyclotetrasiloxane, decamethylcyclopentasiloxane, and dodecamethylcyclohexasiloxane. These cyclic polydimethylsiloxanes generally have a degree of polymerization of 3 to 7. In addition, it is also possible to use cyclic polymethylhydrogensiloxanes, cyclic polymethylvinylsiloxanes, and cyclic polymethylphenylsiloxanes, with low degree of polymerization. Such other cyclic silicones are also known in the cosmetic and silicone industry.

The silicone elastomer used in the oxidation hair dyeing agent composition of this invention is also a material known in the cosmetic industry generally referred to for example as Dimethicone Crosspolymer. Some representative examples are elastomeric polymethylsiloxanes obtained by crosslinking, and which contain alkyl groups with 3–20 carbon atoms. Again, reference may be had to the CTFA's International Cosmetic Ingredient Dictionary. Some other suitable silicone elastomers which can be used include materials obtained by crosslinking polymethylvinylsiloxane and polymethylhydrogensiloxane in the presence of a platinum catalyst; materials obtained by crosslinking $\alpha,\omega$-dihydroxypolydimethylsiloxane with an hydrolyzable group-containing organosilane; and materials obtained by crosslinking polymethylvinylsiloxane in the presence of an organic peroxide. Representative silicone elastomers are also described in U.S. Pat. Nos. 5,654,362, 5,811,487, 5,880,210, and 5,969,035.

If desired, the cyclic silicone can be included as a separate component, or in a mixture with the silicone elastomer. Its content in a mixture with the silicone elastomer is preferably at least about 87 percent by weight, but its content may vary above or below this amount depending on the type and properties of the particular cyclic silicone used, as well as on the type and properties of the silicone elastomer. The cyclic silicone should, however, be readily miscible with other oily like ingredients included in the oxidation hair dyeing agent, and it should be easily emulsifiable in water under influence of an emulsifying agent. Thus, the mixture should exhibit a paste-like or soft gel-like consistency.

If there is too small an amount of the cyclic silicone, the mixture will not exhibit a paste-like or soft gel-like consistency. If there is too small an amount of silicone elastomer, then the corresponding amount of silicone elastomer available to adhere to the hair will be too small, with the result that it will be difficult to impart gloss and smoothness. Thus, the amount of cyclic silicone present can vary from 15–95 percent by weight, the remainder being the silicone elastomer.

The content of cyclic silicone and silicone elastomer in hair dyeing agent compositions of the invention is most preferably about 1.25 percent by weight, based on the total weight of the hair dyeing agent composition. If the amount is too large, then emulsification in water is difficult. If the content is too small, it is difficult to obtain any meaningful hair treatment effect. However, for most purposes, it has been found that the content can vary between 0.1–10 percent by weight. In addition, because the combination of cyclic silicone and silicone elastomer is oil-soluble, the combination is preferably emulsified in water using an emulsifying agent.

The hair dyeing component of the composition of this invention is an oxidation dye precursor, and it can be an indole or indoline such as are described in Japanese Kokai Patent Application Publication No. 08[1996]-040857/U.S. Pat. No. 5,690,697 (November 1997). In addition, some examples of other types of oxidation dye precursors useful in the present invention include compounds such as p-phenylenediamine, p-nitro-o-phenylenediamine, p-chloro-phenylenediamine, p-nitro-m-phenylenediamine sulfate, and other phenylenediamines; toluene-2,5-diamine, toluene-3,4-diamine, toluene-2,5-diamine sulfate, 2,4-diaminophenoxyethanol chloride, and other diamines; p-aminophenol, p-methylaminophenol, m-aminophenol-o-aminophenol, 5-(2-hydroxyethylamino)-2-methylphenol and other aminophenols; aminonitrophenol, 4,4'-diaminophenylamine, and other diphenylamines; diaminophenylamines, N-phenyl-p-phenylenediamine, and other N-phenylphenylenediamines; 2,6-diaminopyridine, 2,5-diaminopyridine, and other diaminopyridines; p-amino-o-cresol and other aminocresols; resorcinol; pyrogallol; phloroglucinol; catechol; and salts thereof.

While there are no particular limitations on the amount of oxidation dye precursor used, it should be present in amounts typically used in such applications, i.e., generally 0.05–10 percent by weight based on the weight of the hair dyeing agent composition.

The oxidation hair dyeing agent composition of the invention can be in a single-component form or a multi-component form made up of two or more agents. As a two-component form, for example, a suitable composition would include a two-part composition used by mixing at the time of hair dyeing, a first agent containing the oxidation dye, cyclic silicone, and silicone elastomer, with a second agent containing an oxidation agent. Alternatively, it could be in the form of a two-part composition used by mixing at the time hair dyeing, a first agent containing an oxidation dye, with a second agent containing the silicones and an oxidation agent. The ratio used for mixing together the first agent with the second agent should be 1:1, but other ratios can be employed, provided they do not result in any adverse effects such as sagging, usability, or levelness of dyeing.

Any conventional oxidation agent can be used for the oxidation hair dyeing agent composition according to this invention. Some examples of suitable oxidation agents are set forth in Japanese Kokai Patent Application Publication No. Hei 08[1996]-040851, referred to above. Thus, some representative and useful compositions include hydrogen peroxide, persulfuric acid salts, perboric acid salts, bromic acid salts, periodic acid salts, urea peroxide, percarbonic acid salts, peroxytripolyphosphoric acid salts, peroxybi-phosphoric acid salts, and peroxyorthophosphoric acid salts. The most preferred oxidation agent based on its ease of use and general availability is a hydrogen peroxide solution.

Other ingredients can be included in the hair dyeing agent composition of the invention provided the effects of the invention are not compromised. Some examples may be found in Japanese Kokai Patent Application Publication No. Hei 08[1996]-040851, referred to above. Representative ingredient include materials compatible with the first agent such as glycerin, propylene glycol, dipropylene glycol, polyethylene glycol, hyaluronic acid salts, diglycerin, 1,2-butylene glycol, pyrrolidone carboxylic acid salts, sorbitol, lactose, oligosaccharides, lanolin, squalane, liquid paraffin, Vaseline, higher fatty acids, triglycerides, and ester oils.

Additional examples of other ingredients are thioglycolic acid salts, L-ascorbic acid salts, hydrogen sulfites, hydrosulfites, hydrogen sulfates, and other anti-oxidants and stabilizers; collagen hydrolyzate, gelatin hydrolyzate, silk protein hydrolyzate, elastin hydrolyzate, soybean protein hydrolyzate, and other protein hydrolyzates and their quaternary derivatives; ammonia water, alkanolamine, ammonium carbonate, sodium hydrogen carbonate, potassium hydroxide, and other alkali agents.

Because combinations including cyclic silicones, silicone elastomers, and other oil-soluble ingredients, are not easily dissolved in water, it is preferred to emulsify these materials in water using an emulsifying agent. Some examples of suitable nonionic surface active agents are polyoxyethylene alkyl ethers, polyoxyethylene fatty acid esters, polyoxyethylene polyhydric alcohol fatty acid partial esters, polyoxyethylene hardened castor oil derivatives; octylpolyglycoside; polyglycerin fatty acid esters, polyglycerin alkyl ether; maltitol hydroxyalkyl ether, other sugar-alcohol hydroxyalkyl ethers; and fatty acid diethanolamide. Some anionic surface active agents which can be used include higher fatty acid salts, alkylbenzenesulfonic acid salts, phosphoric acid esters, alkylsulfuric acid salts, alkylsulfuric acid esters, and polyoxyethylene alkylsulfuric acid esters. Representative cationic surface active agents are amino acids, alkyltrimethylammonium salts, dialkyldimethylammonium salts, and alkyldimethylamine oxides. Mixtures of these surface active agents may also be employed.

Still further examples of other ingredients which can be included with the first agent are ethanol, butanol, propanol, isopropanol, benzyl alcohol, and other lower alcohols; 2-ethylhexyl alcohol, 2-hexyldecyl alcohol, 2-decyltetradecyl alcohol, isostearyl alcohol, cetostearyl alcohol, lauryl alcohol, stearyl alcohol, cetyl alcohol, and other higher alcohols; hydroxyethane diphosphonic acid, phenacetin, EDTA, and salts thereof; parabens, stannates, and other sequestering agents and anti-septic agents; poly (dimethylallyl ammonium halide)-type cationic polymers, cationic polymers formed by condensation of tallowyl amine obtained from beef tallow fatty acids, propyleneamine, epichlorhydrin, and polyethylene glycol; cationic polymers formed by condensation of cocoyl amine obtained from coconut oil fatty acids, propyleneamine, epichlorhydrin, and polyethylene glycol; cationic polymers of dimethylamino methacrylate copolymer; cationic polymers of cellulose ether containing quaternary nitrogen; lauric acid diethanolamide, carboxymethyl cellulose, carboxyvinyl polymer, hydroxyethyl cellulose, hydroxypropyl cellulose, methyl cellulose, xanthan gum, carrageenan, alginic acid salts, pectin, furcellaran, gum arabic, tragacanth gum, agar, bentonite, cross-linkable polyacrylic acid salts, and other such thickeners; pH adjusting agents, fragrances, plant extracts, and drugs.

Some examples of ingredients suitable for combining with the second agent include phenacetin, EDTA, and their salts; parabens, stannates, and other sequestering agents and anti-septic agents; liquid paraffin, Vaseline, and other oily ingredients; 2-ethylhexyl alcohol, 2-hexyldecyl alcohol, 2-decyltetradecyl alcohol, isostearyl alcohol, cetostearyl alcohol, lauryl alcohol, stearyl alcohol, cetyl alcohol, and other higher alcohols; polyoxyethylene alkyl ethers, alkylsulfuric acid ester salts, acylmethyl taurine, and other surface active agents; acids such as citric acid, malic acid, acetic acid, lactic acid, oxalic acid, tartaric acid, formic acid, levulinic acid, and other organic acids; phosphoric acid, hydrochloric acid, and other inorganic acids; pH-adjusting agents, fragrances, plant extracts, drugs, dyes, and water. If it is desired to include the cyclic silicone and silicone elastomer in the second agent instead of, or in addition to the first agent, the silicones should be emulsified in water using an emulsifying agent.

The dyeing process is carried out by applying the oxidation hair dyeing agent composition of the invention to hair, and after allowing the oxidation hair dyeing agent composition to penetrate into the hair, it should remain on the hair for 5 to 30 minutes, preferably about 10 to 20 minutes, at normal temperature in the range of 15–40° C. The hair should then be washed with shampoo or soap containing water, and rinsed with water to wash away any remaining oxidation hair dyeing agent composition.

EXAMPLES

The following application examples are set forth in order to illustrate this invention in more detail.

Application Example 1 & Comparative Examples 1~5

A first hair dyeing agent was prepared by mixing together the ingredients shown in Table 1. In Table 1, p-phenylenediammine, resorcinol, p-aminophenol, m-aminophenol, and 2,4-diaminophenol sulfate, were used as oxidation dye precursors. The first hair dyeing agent had a gel and cream-like appearance.

A first molten oil phase was prepared by mixing together (i) a silicone elastomer in the form of a paste-like mixture containing about 87 percent by weight of Cyclomethicone and about 13 percent by weight of Dimethicone crosspolymer, and (ii) a composition containing about 50 percent by weight of Cyclomethicone and about 50 percent by weight of trimethylsiloxysilicate. The molten oil phase was emulsified in an aqueous solution using an emulsifying agent. A second water soluble phase was prepared by combining (i) a silicone polyether, (ii) a nonionic emulsion containing about 35 percent by weight of an amino-modified silicone polymer, and (iii) a cationic emulsion containing about 35 percent by weight of an amino-modified silicone polymer. The two phases were combined and then added to 5 percent by weight of water and used as the second agent.

Oxidation hair dyeing agent compositions were prepared by mixing the first agent and the second agent, and an aqueous solution containing hydrogen peroxide, in a ratio of 1:1.5. A bundle of hair was treated with each composition, respectively, and the initial color tone and washing resistance were evaluated by a panel of ten volunteers. These evaluations are shown in Table 2.

Color Tone Evaluation & Washing Resistance Testing

The color tone of a bundle of hair treated with an oxidation hair dyeing agent composition in the unwashed condition, and one obtained after washing 5, 10, 15, or 20 times, were evaluated on a nine-point scale from 0 indicating dark to 8 indicating light. An average value was computed for each of the ten panelists.

TABLE 1

| Ingredient, weight % | App. Ex. 1 | Comp. Ex. 1 | Comp. Ex. 2 | Comp. Ex.3 | Comp. Ex. 4 | Comp. Ex. 5 |
| --- | --- | --- | --- | --- | --- | --- |
| Cetyl alcohol | 2.50 | 2.50 | 2.50 | 2.50 | 2.50 | 2.50 |
| Stearyl alcohol | 2.50 | 2.50 | 2.50 | 2.50 | 2.50 | 2.50 |
| ORESU-30 polyoxyethylene (30) oleyl ether | 3.60 | 3.60 | 3.60 | 3.60 | 3.60 | 3.60 |
| Oleic acid | 2.70 | 2.70 | 2.70 | 2.70 | 2.70 | 2.70 |
| Oil/cetyl alcohol 80/85 | 2.50 | 2.50 | 2.50 | 2.50 | 2.50 | 2.50 |
| Ethylene glycol monostearate | 1.00 | 1.00 | 1.00 | 1.00 | 1.00 | 1.00 |
| Polyquaternium 7, copolymer of dimethyl diallyl ammonium chloride & acrylamide | 3.00 | 3.00 | 3.00 | 3.00 | 3.00 | 3.00 |
| 40% aqueous solution of pentasodium salt of diethylene triamine pentaacetic acid | 1.80 | 1.80 | 1.80 | 1.80 | 1.80 | 1.80 |
| Sodium pyrosulfite | 0.60 | 0.60 | 0.60 | 0.60 | 0.60 | 0.60 |
| Sodium erythorbate | 0.20 | 0.20 | 0.20 | 0.20 | 0.20 | 0.20 |
| Mono-ethanolamine, 99 percent | 0.66 | 0.66 | 0.66 | 0.66 | 0.66 | 0.66 |
| Propylene glycol | 5.00 | 5.00 | 5.00 | 5.00 | 5.00 | 5.00 |
| Carbopol ® EDT 2020, carboxyvinyl polymer | 0.30 | 0.30 | 0.30 | 0.30 | 0.30 | 0.30 |
| Rheology adjusting agent | 1.00 | 1.00 | 1.00 | 1.00 | 1.00 | 1.00 |
| Ammonia water, 27% | 10.02 | 10.02 | 10.02 | 10.02 | 10.02 | 10.02 |

TABLE 2

| Ingredient, weight percent | Appl. Ex. 1 | Comp. Ex. 1 | Comp. Ex. 2 | Comp. Ex. 3 | Comp. Ex. 4 | Comp. Ex. 5 |
| --- | --- | --- | --- | --- | --- | --- |
| p-phenylene-diamine | 0.28 | 0.28 | 0.28 | 0.28 | 0.28 | 0.28 |
| Resorcinol | 0.44 | 0.44 | 0.44 | 0.44 | 0.44 | 0.44 |
| p-aminophenol | 0.02 | 0.02 | 0.02 | 0.02 | 0.02 | 0.02 |
| m-aminophenol | 0.05 | 0.05 | 0.05 | 0.05 | 0.05 | 0.05 |

TABLE 2-continued

| Ingredient, weight percent | Appl. Ex. 1 | Comp. Ex. 1 | Comp. Ex. 2 | Comp. Ex. 3 | Comp. Ex. 4 | Comp. Ex. 5 |
| --- | --- | --- | --- | --- | --- | --- |
| 2,4-diaminophenol sulfate | 0.0308 | 0.0308 | 0.0308 | 0.0308 | 0.0308 | 0.0308 |
| Mixture of Cyclomethicone and Dimethicone crosspolymer | 1.25 | | | | | |
| Mixture of Cyclomethicone and trimethylsiloxy silicate | | | 1.25 | | | |
| Amino-modified silicone cationic emulsion | | | | 3.57 | | |
| Amino-modified silicone nonionic emulsion | | | | | 3.57 | |
| Polyether modified silicone | | | | | | 1.25 |
| Water | Balance | Balance | Bal. | Bal. | Bal. | Bal. |

TABLE 3

| Times Washed | Appl. Ex. 1 | Comp. Ex. 1 | Comp. Ex. 2 | Comp. Ex. 3 | Comp. Ex. 4 | Comp. Ex. 5 |
| --- | --- | --- | --- | --- | --- | --- |
| 0 | 6.29 | 6.40 | 6.21 | 6.21 | 6.31 | 6.34 |
| 5 | 6.20 | 6.63 | 6.30 | 6.33 | 6.18 | 6.50 |
| 10 | 6.25 | 6.68 | 6.50 | 6.33 | 6.28 | 6.55 |
| 15 | 6.38 | 7.08 | 6.70 | 6.70 | 6.35 | 6.68 |
| 20 | 6.45 | 7.23 | 6.90 | 6.75 | 6.70 | 6.98 |

As can be seen in Table 2, hair dyed using the oxidation hair dyeing agent composition of the invention exhibited practically no discoloration even after repeated washing and had superior washing resistance, while the hair dyed using the oxidation hair dyeing agent composition of the comparative examples exhibited discoloration after repeated washing and had inferior washing resistance. Because the hair dyeing agent composition of the invention contains a cyclic silicone and a silicone elastomer, hair dyed using the composition possesses deep color tones, exhibits no discoloration even after repeated washings, and has superior washing resistance.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. An oxidation hair dyeing agent composition comprising a mixture of an oxidation dye precursor, a cyclic silicone, and a silicone elastomer, the silicone elastomer being an elastomeric polymethylsiloxane obtained by crosslinking wherein the content of cyclic silicone and silicone elastomer vary between 0.01–10% by weight based on the total weight of the hair dyeing agent composition.

2. The composition according to claim 1 in which the oxidation dye precursor is a compound selected from the group consisting of p-phenylenediamine, p-nitro-o-phenylenediamine, p-chlor-o-phenylenediamine, p-nitro-m-phenylenediamine sulfate, toluene-2,5-diamine, toluene-3,4-diamine, toluene-2,5-diamine sulfate, 2,4-diaminophenoxyethanol chloride, p-aminophenol, p-methylaminophenol, m-aminophenol-o-aminophenol, 5-(2-hydroxyethylamino)-2-methylphenol, aminonitrophenol, 4,4'-diaminophenylamine, diaminophenylamines, N-phenyl-p-phenylenediamine, 2,6-diaminopyridine, 2,5-diaminopyridine, p-amino-o-cresol, resorcine, pyrogallol, phloroglucin, catechols, and salts thereof.

3. The composition according to claim 1 wherein the mixture is emulsified in water using an emulsifying agent.

4. A method of dyeing hair comprising applying to hair the composition according to claim 1.

5. A two-component oxidation hair dyeing agent composition comprising as the first component a mixture of an oxidation dye precursor, a cyclic silicone, a silicone elastomeric polymethylsiloxane obtained by crosslinking wherein the content of cyclic silicone and silicone elastomer vary between 0.01–10% by weight based on the total weight of the hair dyeing agent composition, an emulsifying agent, and water, the mixture being emulsified in water using said emulsifying agent; and a second component being an aqueous hydrogen peroxide solution.

6. A method of dyeing hair comprising applying to hair the composition according to claim 5.

* * * * *